(12) United States Patent
Balbo Block et al.

(10) Patent No.: US 9,120,827 B2
(45) Date of Patent: Sep. 1, 2015

(54) RELEASE AGENT AND USE FOR THE PRODUCTION OF COMPOSITE MOULDINGS

(75) Inventors: Maike Vivian Balbo Block, Hamburg (DE); Thomas Lüthge, Consrade (DE); Nadine Habeck, Schönberg (DE)

(73) Assignee: EVONIK DEGUSSA GMBH, Essen (DE)

( * ) Notice: Subject to any disclaimer, the term of this patent is extended or adjusted under 35 U.S.C. 154(b) by 68 days.

(21) Appl. No.: 12/958,782

(22) Filed: Dec. 2, 2010

(65) Prior Publication Data

US 2011/0139387 A1 Jun. 16, 2011

(30) Foreign Application Priority Data

Dec. 10, 2009 (DE) .................. 10 2009 047 764

(51) Int. Cl.
| | | |
|---|---|---|
| *C07F 9/09* | (2006.01) | |
| *B29C 33/62* | (2006.01) | |
| *C08G 18/76* | (2006.01) | |
| *C08L 97/02* | (2006.01) | |

(52) U.S. Cl.
CPC .............. *C07F 9/091* (2013.01); *B29C 33/62* (2013.01); *C07F 9/098* (2013.01); *C08G 18/7664* (2013.01); *C08L 97/02* (2013.01)

(58) Field of Classification Search
CPC ..... C08L 97/02; C08L 2666/20; C08L 61/06; C08L 61/24; C08L 61/28; C08L 63/00; C08L 67/02; C08L 67/04; C08L 75/04; B29C 33/62; C07F 9/091; C07F 9/098; C08G 18/7664
USPC ....................................... 106/38.2
See application file for complete search history.

(56) References Cited

U.S. PATENT DOCUMENTS

| | | | |
|---|---|---|---|
| 3,337,441 A | 8/1964 | Goldsmith | |
| 3,151,016 A | 9/1964 | Kutik et al. | |
| 3,440,189 A | 4/1969 | Sharp | |
| 4,257,995 A | 3/1981 | McLaughlin et al. | |
| 4,257,996 A | 3/1981 | Farrissey, Jr. et al. | |
| 4,369,134 A * | 1/1983 | Deguchi et al. ............... 510/404 |
| 4,462,922 A | 7/1984 | Boskamp | |
| 4,865,646 A | 9/1989 | Egberg | |
| 5,008,359 A | 4/1991 | Hunter | |
| 5,140,086 A | 8/1992 | Hunter et al. | |
| 5,204,176 A | 4/1993 | Seiss et al. | |
| 6,274,150 B1 * | 8/2001 | Simonnet et al. ............. 424/401 |
| 6,420,034 B1 | 7/2002 | Takahashi et al. | |
| 6,471,905 B1 | 10/2002 | Haas et al. | |
| 2003/0020210 A1 | 1/2003 | Robinson et al. | |
| 2007/0059505 A1 * | 3/2007 | Williams et al. ........... 428/292.1 |
| 2008/0004357 A1 | 1/2008 | Meyer et al. | |

FOREIGN PATENT DOCUMENTS

| | | |
|---|---|---|
| CN | 1284972 A | 2/2001 |
| DE | 2932175 | 4/1980 |
| DE | 3108537 A1 | 11/1982 |
| DE | 19601401 C1 | 5/1997 |
| DE | 10340684 A1 | 7/2004 |
| DE | 10337594 A1 | 3/2005 |
| DE | 102006030532 A1 | 1/2008 |
| EP | 0057502 B1 | 6/1984 |
| EP | 0046014 | 11/1985 |
| EP | 0269869 A2 | 6/1988 |
| EP | 0129430 | 1/1990 |
| EP | 0460858 A1 | 12/1991 |
| EP | 1038898 A1 | 9/2000 |
| EP | 1719597 A1 | 11/2006 |
| GB | 1148016 | 4/1969 |
| WO | WO9800464 | 1/1998 |
| WO | WO0053381 | 9/2000 |
| WO | WO0158998 A1 | 8/2001 |
| WO | WO0236268 A1 | 5/2002 |
| WO | WO03008164 A2 | 1/2003 |
| WO | WO03072324 A1 | 9/2003 |

OTHER PUBLICATIONS

European Search Report dated Mar. 16, 2011.
European Search Report dated Sep. 12, 2012 received in a corresponding foreign application.
Russian Office Action dated Dec. 3, 2014, received in a corresponding foreign application.
English-language translation of a Chinese Office Action dated Dec. 4, 2013 received in a corresponding foreign application.

* cited by examiner

*Primary Examiner* — Shuangyi Abu Ali
(74) *Attorney, Agent, or Firm* — Scully, Scott, Murphy & Presser, P.C.

(57) ABSTRACT

A release agent composition is provided which contains as components:
  a) at least one phosphate
  and
  b) at least one compound having at least two hydroxyl groups and having a molecular weight of less than 250 g/mol, the proportion of the component a), based on the composition, being from 0.1 to 70% by weight and the proportion of component b) being from 0.5 to 90% by weight. A process for the production of composite moldings in which the release agent composition is used, composite moldings obtainable in a corresponding manner and the use thereof also described.

9 Claims, No Drawings

RELEASE AGENT AND USE FOR THE PRODUCTION OF COMPOSITE MOULDINGS

FIELD OF THE PRESENT APPLICATION

The present application relates to a release agent and its use for the production of composite mouldings by reacting optionally modified organic binders with materials in the form of chips, fibres, mats or granules, in particular cellulose-containing materials, such as, for example, wood, flax or straw, in an open or closed mould. The mould release agent of the present application includes at least one phosphate of the formula I and alcohols.

BACKGROUND

The production of compressed shaped articles designated as "composites" from wood pieces, fibres or particles, such as, for example, OSB (oriented strand boards), chipboards, fibreboards, such as, for example, MDF or HDF boards (medium-density or high-density fibreboards) or plywood, as well as cork boards and mouldings comprising flax, straw or other cellulose-containing materials, with isocyanate binders, optionally in the presence or absence of catalysts, auxiliaries and/or additives in an open or closed mould is disclosed in numerous patent and literature publications. See, for example, WO 98/00464, U.S. Pat. No. 5,008,359, U.S. Pat. No. 5,140,086, U.S. Pat. No. 5,204,176, and U.S. Pat. No. 3,440,189.

In these prior art processes, temperatures of 20° C. to 450° C. are necessary, depending on the binder, in order to ensure the reaction of the binders and to permit shaping of the materials to give the desired final shape, such as, for example, planks or boards. Pressures of 0 to 100 bar are reached during this procedure.

The proportion by mass of the binders, based on the total weight of the mouldings, is 1 to 80% by weight, preferably 5 to 40% by weight and in particular less than 20% by weight, depending on the type of binder used and the type of composite.

Binders used in the aforementioned prior art processes are all types of polyfunctionalized isocyanates, typically aromatic polyisocyanates. The most widely used aromatic polyisocyanate is polymeric diphenylmethane diisocyanate (PMDI). In addition to the isocyanates, various formaldehyde resins are used as binders for composite mouldings. The most common ones include urea/formaldehyde, phenol/formaldehyde or melamine/formaldehyde resins and mixtures of these. Binders comprising renewable raw materials, such as tannins, lignins or proteins, are also used in small amounts. Furthermore, casting resins, such as, for example, epoxy, polyester, polyurethane or polylactide resins, are used.

Although the production of compact cellulose/isocyanate mouldings has acquired considerable industrial importance, the prior art processes described also have technical deficiencies because of the outstanding adhesion of polyurethanes to other materials. What is particularly disadvantageous is that the mouldings adhere to the moulds and are therefore difficult to remove from the moulds, which frequently leads to damage to the mouldings, in particular to the surface thereof. In order to avoid this disadvantage, as a rule polished, metallic moulds are used and/or release agents are employed.

Either these mould release agents are used as internal lubricants in the curable cellulose-isocyanate mixture or the internal mould surfaces are provided with a uniform coating of external lubricants before the production of the mouldings, for which purpose various injection and spray methods and roll-coating methods (DE-10 337 594) are known from the prior art. It is also possible for the surface of the particles to be moulded to be coated with mould release agent. This is likewise performed by spray application.

Conventional internal or external lubricants used are, for example, fatty acids and the metal salts thereof (see, for example, WO-A-03/072324, and WO-A-02/36268), polymeric fatty acids (see, for example, EP-A-0 269 869), carboxy-functionalized siloxane (see, for example, EP-B-0 129 430), waxes (see, for example, EP-B-0 046 014), especially ester wax (see, for example, EP-B-0 057 502), oxidized wax (see, for example, WO-A-00/53381) or polyolefin wax (see, for example, WO-A-98/00464), polyolefin wax in combination with fatty acids (see, for example, WO-A-01/58998) or finally fatty acids or wax acids in combination with polysiloxanes, which are modified with an organically bonded active hydrogen group and are capable of reacting with isocyanate (see, for example, WO-A-03/008164).

Such conventional release agents have the disadvantage that the finished mouldings have dark discolorations on the surface, which greatly impair the optical value of the finished mouldings. Furthermore, compression moulds frequently show a build up of black residues.

These build-up residues can also accumulate again on the mouldings produced and in this way also lead to dark discolorations and/or irregularities in the surface structure thereof or, particularly in the case of silicone-containing release agents, can lead to considerable coating problems. As a result, an aftertreatment, such as, for example, grinding of the surface, is necessary in some cases.

DE 19601401 describes talc as a thermally stable release material in the production of shaped cellulose-isocyanate-containing articles. However, this inorganic solid is solid at the compression temperature and thus likewise leads to considerable build-up on the compression moulds.

EP 1 719 597 describes the use of siloxane compounds containing aminopropyl groups as mould release agents for avoiding the build up of black residues.

GB 1148016 describes, as release materials, organic substances which contain free hydroxyl groups, i.e., polyols, such as glycerol, ethylene glycol, polyesters or polyethers. However, because of their hydroxyl groups, these substances react with the isocyanate used as binder and cannot alone act as a substance having release activity.

DE 2932175, U.S. Pat. No. 4,257,995 and DE 3108537 describe release agents which contain acid phosphate esters as substances having release activity, in particular as internal lubricants, for use in production of (ligno)cellulose-containing products.

In the course of increasing optimization in the production of composite mouldings, there is however still a need for increasing the processing speeds and reducing the processing temperatures.

SUMMARY

An object of the present application was therefore to provide a release agent which avoids one or more disadvantages of the release agents of the prior art and which preferably permits an increase in the processing speeds and/or a reduction of the processing temperatures.

Surprisingly, it has now been found that the object of the present application is achieved by addition of at least one compound having at least two hydroxyl groups and having a molecular weight of less than 250 g/mol, such as, for example, monoethylene glycol or glycerol, to phosphates, as partly described, for example, in DE 2932175, U.S. Pat. No. 4,257,995 and DE 3108537 as substances having release activity.

The present application therefore relates to release agent compositions, the use thereof in the process for the production of composite mouldings, the composite mouldings themselves obtainable by the process according to the present application and the use thereof as described in detail in the description that follows.

The release agent of the present application has the advantage that the processing speed, in particular in continuous production processes, can be considerably increased by its use.

The release agent according of the present application also has the advantage that its use permits lower processing temperatures. In addition to energy saving, this also enables wood (chip) boards, for example produced at lower temperatures, to be produced in lighter shades.

Even at higher processing temperature the release agent compositions of the present application have the advantage that discolorations and/or dark colorations of the surfaces of the composite mouldings produced do not occur or occur only to a slight extent.

DETAILED DESCRIPTION

The release agent compositions according to the present application, the use thereof in processes for the production of composite mouldings, the composite mouldings themselves and the use thereof are described by way of example below without there being any intention to limit the present application to these exemplary embodiments. Where ranges, general formulae or classes of compounds are mentioned below, these are intended to comprise, not only the corresponding ranges or groups of compounds which are explicitly mentioned, but also all partial ranges and partial groups of compounds which can be obtained by eliminating individual values (ranges) or compounds. Where documents are cited in the present description, the content thereof, particularly regarding the facts referred to, is to be completely incorporated in the disclosure content of the present application. Unless stated otherwise, data in percent always mean mass %. Where mean values are mentioned below, these are the number-average mean values, unless stated otherwise.

The release agent compositions of the present application are distinguished in that such compositions contain at least the following components a. at least one phosphate of the general formula (Ia)

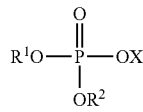

(I)

where

X=$R^6$, H, metal, preferably alkali metal, preferably Na or K, or alkaline earth metal, such as, for example, Mg, Ba, Sr or Ca, preferably Ca, $NR_zH_{4-z}^+$, where z=0 to 4, preferably 2 or 3, and R=hydrocarbon radical having 1 to 10, preferably 1 to 4, carbon atoms or a radical of the formula (II)

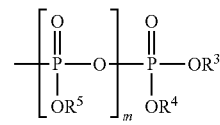

(II)

where m=0 to 5, and $R^1$ to $R^6$, independently of one another, are hydrogen, a metal, preferably an alkali metal, such as, for example, sodium or potassium, or an alkaline earth metal, such as, for example, Mg, Ba, Sr or Ca, preferably Ca, or $NR_zH_{4-z}^+$, where z and R are as described above, or an organic radical, and b. at least one compound having at least two hydroxyl groups and having a molecular weight of less than 250 g/mol, the proportion of the component a), based on the composition, being from 0.1 to 70% by weight, preferably from 1 to 20, more preferably from 2 to 10, % by weight and the proportion of the component b) being from 0.5 to 90% by weight.

In some embodiments of the present application, it may be advantageous if the mass ratio of component a) to component b) is from 20:80 to 80:20, preferably from 40:60 to 60:40 and particularly preferably about 50:50.

As component b), the composition of the present application preferably contains one or more diols, triols and/or polyhydric polyols, preferably one or more compounds selected from the group consisting of monoethylene glycol, diethylene glycol, triethylene glycol, tetraethylene glycol, propylene glycol, butylene glycol, glycerol, trimethylolpropane and pentaerythritol. Particularly preferably, component b) of the composition of the present application consists of one or more compounds selected from the group consisting of monoethylene glycol, diethylene glycol, triethylene glycol, tetraethylene glycol, propylene glycol, butylene glycol, glycerol, trimethylolpropane and pentaerythritol.

If the radicals $R^1$ to $R^6$ are organic radicals, the radicals may be identical or different. The organic radicals $R^1$ to $R^6$ are preferably selected from branched or straight-chain, acyclic or cyclic, alicyclic or heterocyclic, aliphatic or aromatic or heteroaromatic, substituted or unsubstituted, organic radicals, preferably a linear aliphatic saturated and/or unsaturated radical having 1 to 25, preferably 12 to 18, carbon atoms, or radicals of the formula (III)

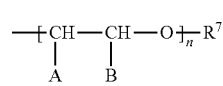

(III)

where $R^7$=a branched or straight-chain, acyclic or cyclic, alicyclic or heterocyclic, aliphatic or aromatic or heteroaromatic, substituted or unsubstituted organic radical, preferably a linear aliphatic saturated and/or unsaturated radical having 1 to 25, preferably 12 to 18, carbon atoms, A or B is hydrogen and the respective other radical is hydrogen or a substituted or unsubstituted, linear or branched alkyl radical having 1 to 10 carbon atoms or an aryl radical, preferably a phenyl radical, preferably a phenyl, ethyl or methyl radical, preferably a methyl radical, and n is a number-averaged number from 1 to 100, preferably 2 to 10.

If one or more of the radicals $R^1$ to $R^7$ is, or are, a cyclic radical, in particular an alicyclic hydrocarbon radical, this may be, for example, a cycloalkyl or cycloalkenyl radical. If one or more of the radicals $R^1$ to $R^7$ is, or are, a heterocyclic radical, this preferably has nitrogen, carbon and optionally further heteroatoms. The heterocyclic radical may be, for example, a three-, four-, five-, six- or higher-membered ring which, in turn, may be substituted by H, alkyl or aryl groups with acceptor or donor substituents or parts of cyclic systems with acceptor or donor substituents and/or hydrophilic or hydrophobic groups. Particularly preferably, the heterocyclic radical is a pyrrolidinyl, pyrrolinyl, piperidinyl or morpholinyl radical. If one or more of the radicals $R^1$ to $R^7$ is, or are, an aryl radical, this may be, for example, a phenyl, naphthyl or anthracenyl radical. If one or more radicals $R^1$ to $R^7$ is, or are, a heteroaryl radical, this may preferably be an imidazolyl, pyrazolyl, pyridinyl, thienyl, thiazolyl, furyl or indolyl radical. The radicals $R^1$ to $R^7$ may also be those organic radicals in which one or more of the radicals $R^1$ to $R^7$ are linked to one another.

It may be advantageous if at least one inorganic phosphate, in which $R^1$ and $R^2$ or, if applicable (when X=radical of the formula (II)), $R^1$ to $R^5$ are not organic radicals, is present as component a). Preferred inorganic phosphates are those in which X is a radical of the formula (II) and in which m=1 to 3, preferably 1 or 2, and the radicals $R^1$ to $R^5$ are identical or different and are H, $NH_4^+$, K or Na, preferably Na.

It may furthermore be advantageous if at least one organic phosphate, in which at least one of the radicals $R^1$ or $R^2$ or, if applicable (if X=radical of the formula (II)), at least one of the radicals $R^1$ to $R^5$ is not H, metal or $NR_zH_{4-z}^+$, where R and z are defined as above, is present as component a). Preferred organic phosphates are those of the formula (I) in which X=H, $NH_4^+$, K or Na, in particular K, and at least one or both of the radicals $R^1$ or $R^2$, preferably only one of the radicals, is an alkyl or alkenyl radical, preferably an alkyl or alkenyl radical having 10 to 25, preferably 12 to 18, carbon atoms, particularly preferably an oleyl or stearyl radical, and the other radical is optionally H, $NH_4^+$, K or Na, in particular K.

Preferred compositions of the present application are those which contain, as component a), at least one inorganic phosphate, in which $R^1$, $R^2$ and X, or if applicable (if X=radical of the formula (II)), $R^1$ to $R^5$ are not organic radicals, and at least one organic phosphate, in which at least one of the radicals $R^1$, $R^2$ or X or, if applicable (if X=radical of the formula (II)), at least one of the radicals $R^1$ to $R^5$ is not H, metal or $NR_zH_{4-z}^+$, where R and z are as defined above.

Particularly preferred compositions of the present application are those which have no phosphate of the formula (I), in which all radicals $R^1$, $R^2$ and X or, if applicable (if X=radical of the formula (II)), all radicals $R^1$ to $R^6$ are organic radicals, as component a).

Very particularly preferred compositions of the present application are those which contain an alkali metal polyphosphate, e.g., sodium tripolyphosphate, and/or alkali metal mono- and/or dialkyl or alkenyl phosphate, e.g., potassium mono-/dioleyl phosphate, as component a).

It may be advantageous if the composition of the present application has an alkali metal hydroxide as component c). Preferably, the composition contains an alkali metal hydroxide selected from NaOH and KOH, preferably in the form of an aqueous solution, as component c).

The release agent composition of the present application or, if the release agent composition contains no water, in an aqueous solution of 10% by weight of release agent composition in water, preferably has a pH, measured by means of pH test strips (which are available for the pH range from 7.5 to 9.5, e.g. from Marcherey-Nagel as pH-Fix 7.5-9.5), of greater than or equal to 7 to 14, preferably 7 to 10 and particularly preferably 8 to 9. The pH of the composition can be adjusted by addition of alkali metal hydroxide (solution), organic acids, such as, for example, acetic acid, and/or mineral acids, preferably phosphoric acid.

Components a) and b) can be used in pure form as a release agent. However, since components a) and b) show outstanding release results even in low concentrations, it is advantageous if the release agent composition also has a solvent. The release agent composition of the present application thus may have an organic or inorganic, preferably inorganic, solvent, preferably water, as component d). Preferred release agent compositions have a proportion of solvent, preferably water, of 1 to 99% by weight, preferably 80 to 98% by weight and particularly preferably of 85 to 97% by weight.

Organic solvents are less preferred since such solvents have low ignition points and may ignite in the range of the temperatures of use. Cyclic or linear siloxanes are more suitable; only those siloxanes being considered whose ignition point is above the application temperatures used.

For avoiding large transport volumes, it may be advantageous to store and to transport the release agent composition of the present application without solvent or only with small amounts of solvent and to dilute it to said preferred solvent concentrations only shortly before or during use by addition of solvent.

The composition of the present application may further include customary auxiliaries and additives as component e). In particular, the following may be present as auxiliaries or additives in the composition of the present application:

A) Emulsifiers:

Anionic emulsifiers, such as alkyl ether carboxylates, alkyl sulphates, fatty alcohol ethoxylate ether sulphates, alpha-olefinsulphonates, alkyl phosphates, alkylpolyether phosphates, alkyl sulphosuccinates; nonionic emulsifiers, such as fatty alcohols, ethoxylated fatty alcohols, ethoxylated oxo alcohols and other alcohol ethers, fatty amines, such as dimethylalkylamines, fatty acid alkanolamides, fatty acid esters with alcohols, including glyceryl esters or polyglyceryl esters or sorbitol esters; cationic emulsifiers, such as acidified alkyldimethylamines, quaternary nitrogen compounds; finally, zwitterionic surfactants or combinations of the emulsifiers. The proportion of emulsifiers, based on the total composition of the present application, is preferably from 0.1 to 10% by weight, preferably 0.5 to 6% by weight.

B) Catalysts:

Catalysts which may be used are those which are typically used for the reaction of the binder. Catalysts suitable for the polyurethane reaction may be, for example, Lewis acids, such as, for example, tin compounds, or Lewis bases, such as, for example, tertiary amines. For example, ammonium salts, such as, for example, ammonium sulphate, or peroxides can be used for catalysis in the case of formaldehyde resins used as binders.

C) Viscosity Modifiers:

For example, typical thickeners, such as polyacrylic acid derivatives designated as carbomers, or other polyelectrolyte thickeners, such as water-soluble celluloses or xanthan gum, may be present as viscosity modifiers in the composition of the present application.

D) Preservatives, Bactericides and/or Fungicides.

The preservatives, bactericides and/or fungicides that can be employed include any preservative compound, bactericide compound and/or fungicide compound that are typically employed in moulding applications. These compounds are well known in the art and therefore are not described in detail herein.

E) Commercially Available Antioxidants and Antifoams.

The antioxidants and antifoams that can be employed include any antioxidant compound, and/or antifoam compound that are typically employed in moulding applications. These compounds are well known in the art and therefore are not described in detail herein.

F) Antistatic Agents

Commercially available additives for influencing the conductivity, such as antistatic additives or conductivity-increasing additives.

The composition of the present application may be present as an emulsion and/or dispersion and/or solution.

For the preparation of a composition of the present application, any known method suitable for this purpose may be used.

The release agent compositions of the present application can be used in all processes in which release agents are employed. Preferably, the release agent composition of the present application is used in the below-described process, which represents a process of the present application.

The process of the present application for the production of a composite moulding by continuous or batchwise compression moulding of a mass containing at least one organic binder and at least one material which is present in the form of chips, fibres, mats, powders or granules is distinguished in that the compression moulding is performed in the presence of a release agent composition of the present application.

The process of the present application is preferably carried out in such a way that the compression mould has a temperature of 20° C. to 450° C., depending on the binder, during the compression moulding process. In the case of isocyanates/polyisocyanates and formaldehyde resins, temperatures of 90° C. to 350° C., preferably of 180° C. to 275° C., are preferably used, while temperatures of 20° C. to 150° C. are preferably used when employing epoxy resins as binders.

The release agent composition of the present application can be used as an internal lubricant (incorporation of the release agent composition into the mass to be moulded) or as an external lubricant (application of the release agent composition to the mass to be moulded or to the mould). Preferably, the release agent composition of the present application is used as an external lubricant.

If the release agent composition is used an external lubricant, this is preferably applied by a customary application method, for example, by spraying or roll-coating, to the mass to be moulded or the compression mould or the pressplate.

If the process of the present application is carried out continuously, the shaping is preferably effected by pressplates and/or press rolls. The speed at which the mass to be moulded is moved is preferably from 0.5 to 500 m/min, preferably from 10 to 100 m/min and particularly preferably from 15 to 50 m/min.

In the process of the present application, isocyanates, polyisocyanates, urea/formaldehyde, phenol/formaldehyde, melamine/formaldehyde, epoxy (EP), polyurethane, polyester and/or polylactide resins are preferably used as organic binders. Polyisocyanates, in particular diphenylmethane diisocyanate (MDI) or polymeric diphenylmethane diisocyanate (PMDI), are preferably used as binders.

Preferably a cellulose-containing, preferably lignocellulose-containing material or a material consisting of cellulose, preferably lignocellulose, is used as material for the production of the mass to be moulded.

The process of the present application can be carried out as described in the prior art. Usually, the lignocellulose material is initially introduced in fibre or particle form, binder is then added to give a mass and moulding is then performed in a metal press or by application of reduced pressure/vacuum. The release agents described are sprayed before the compression moulding process either onto the chips or the mass or onto the metal plates, metal rolls or moulds, which may already be hot, as described, for example, in WO-A-02/36268. Finally, the moulded material is removed from the shape-imparting mould.

The composite mouldings of the present application are obtainable by the process described above. These may have, for example, the shape of a board, a block, a beam or an optionally profiled strand. Of course, any possible shapes can be achieved by using corresponding moulds. Preferred composite mouldings are, for example, OSB (oriented strand boards), chipboards, fibreboards, such as, for example, MDF and HDF boards (medium-density and high-density fibreboards, respectively), and plywood, but also cork boards and mouldings comprising flax, straw or other cellulose-containing materials.

The composite mouldings of the present application can be used for the production of pieces of furniture or furniture parts or of packaging materials or as material in house building and interior finishing.

The examples below are intended to describe the subject of the present application in more detail without there being any intention to limit the present application to these embodiments.

EXAMPLES

List of substances used:
ILCOPhos 208=mono-/dioleyl phosphate
Polypray® STPP=sodium tripolyphosphate, manufacturer Prayon
Glycerol=ultrapure glycerol, 87% pure
Hostaphat® MDAH=mono-/di(2-ethylhexyl)phosphate, manufacturer Clariant
Emulsogen® PN Extra=mixture of fatty alcohol polyglycol ethers, manufacturer Clariant
Licowachs® KPE=emulsifier-containing montan ester wax, manufacturer Clariant Example 1

Preparation of the Release Agent Emulsions

Example 1a

Release Agent According to the Present Application 12 g of Hostaphat® MDAH are stirred with 5.4 g of a 50% strength by weight aqueous potassium hydroxide solution and 32.6 g of water to give a dispersion. A solution of 3 g of glycerol and 3 g of Polypray® STPP in 44 g of water was then stirred into the dispersion.

Example 1b

Release Agent According to the Present Application 10 g of sodium tripolyphosphate and 10 g of glycerol (87% pure) were dissolved in 70 g of water and stirred into a dispersion of 2 g of oleyl phosphate, 0.9 g of 50% strength by weight, aqueous potassium hydroxide solution and 10 g of water.

Comparative Example A

Classical Wax-Containing Release Agent

As comparative release agent A, 80 g of Emulsogen® PN Extra with 400 g of Licowachs® KPE were mixed at elevated temperatures with vigorous stirring with 50 g of water and then diluted with 5.47 g of water to give the finished emulsion.

Comparative Example B

As comparative release agent B, 12 g of Hostaphat MDAH and 4.7 g of 50% strength by weight, aqueous potassium hydroxide solution were mixed with vigorous stirring with 50 g of water and then diluted with 33.3 g of water to give the finished emulsion.

Comparative Example C

Based on GB 1148016, Page 3, Line 8

100% of glycerol.

Example 2

Release Experiments

The release agents according to examples 1a and 1b and comparative examples A, B and C were applied by means of a nozzle in amounts of 30 g/m² to the metal presses in the form of metal belts. Wood pieces were mixed with crude diphenylmethane diisocyanate (MDI) and moulded at a temperature of 240° C. The belt speed was 25 m/min, the sheet width was 2.5 m and the board thickness was 11 mm. In a further experiment (run 2), the experiment was repeated at a temperature of 200° C. and a belt speed of 30 m/min with the same board thickness in order to optimize the production conditions. The results of the release experiments are shown in Table 1.

TABLE 1

Rating of the release agent experiments:

| Release agent | Run 1: Appearance of the woodboard surfaces | Run 2: Appearance of the woodboard surfaces |
| --- | --- | --- |
| 1a | Uniform, thoroughly set, light | Uniform, thoroughly set, light |
| 1b | Uniform, thoroughly set, light | Uniform, thoroughly set, light |

TABLE 1-continued

Rating of the release agent experiments:

| Release agent | Run 1: Appearance of the woodboard surfaces | Run 2: Appearance of the woodboard surfaces |
| --- | --- | --- |
| A | Uniform, thoroughly set, generally darker, dark spots | Wood pieces partly split off, generally darker, dark spots |
| B | Uniform, thoroughly set, light | Partial adhesion to the metal plate, light |
| C | Release agent cannot be used, no release effect | Release agent cannot be used, no release effect |

As can be clearly seen from Table 1, the woodboards in the production of which the release agents of the present application are used have no dark spots even at high belt speeds.

Example 3

Laboratory Release Experiments

The release agent compositions shown in Table 2 below were tested under laboratory conditions. For this purpose, the release agent compositions were sprayed onto metal test sheets (10×15 mm) and these were used for compression moulding of chips glue-coated with 4% by weight of PMDI (Desmodur® 44V20, Bayer). The force which was required to remove the resulting moulding from the mould was then measured.

The release properties in the production of the mouldings were measured with the aid of a spring balance. The unit of measure was kg. A force of <0.1 kg corresponds to a very good release effect, a force of 0.1 to 0.5 kg corresponds to a good release effect and a force of 0.5 to 1 kg was satisfactory. The rating is shown in Table 2.

The alcohol used in experiments 3.1 to 3.5 was glycerol. In experiment 3.6, which serves as a comparative example, an ethylene oxide/propylene oxide copolymer, obtainable under the trade name Polyglycole P41 3000 from Clariant, was used as the alcohol.

The polyphosphate used in experiments 3.1 to 3.6 was sodium tripolyphosphate.

The KOH used was a 50% strength by weight, aqueous potassium hydroxide solution.

The phosphate ester used in experiments 3.1 and 3.2 was Ilcophos 208. Hostaphat MDAH was used in experiment 3.4 and Walliphos SPP K, which also contains 30% of potassium monocetyl phosphate, i.e., yet a further ester, in addition to potassium monooleyl phosphate, was used in experiment 3.5.

TABLE 2

Laboratory experiments

| Example | 3.1 | 3.2 | 3.3 | 3.4 | 3.5 | 3.6 |
| --- | --- | --- | --- | --- | --- | --- |
| Alcohol | 10 g | 3 g | 10 g | 4.8 g | 3 g | 10 g |
| Polyphosphate | 10 g | 3 g | 10 g | 4.8 g | 3 g | 5 g |
| Phosphate ester | 2 g | 12 g | — | 0.4 g | 13.5 g | — |
| KOH | 0.5 g | 5.4 g | — | 0.5 g | — | — |
| Water | 77.5 g | 76.6 | 80 g | 39.5 g | 80.5 g | 85 g |
| Release property | Very good | Very good | Good | Satisfactory plus | Very good | Satisfactory minus |

Examples 3.1 to 3.6 show that good results can be obtained with the release agent compositions of the present application and these are better than those of the comparative experiments. It is also evident that those release agent compositions which have a polyphosphate (inorganic phosphate) and a phosphate ester (organic phosphate) have particularly good release properties.

While the present application has been particularly shown and described with respect to various embodiments thereof, it will be understood by those skilled in the art that the foregoing and other changes in forms and details may be made without departing from the spirit and scope of the present disclosure. It is therefore intended that the present application not be limited to the exact forms and details described and illustrated, but fall within the scope of the appended claims.

What is claimed is:

1. A release agent composition comprising:
component a) at least one inorganic phosphate and at least one organic phosphate both of general formula (I)

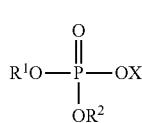

where
X=$R^6$, H, metal, $NR_zH_{4-z}^+$, where z=0 to 4, and R=hydrocarbon radical having 1 to 10 carbon atoms or a radical of formula (II)

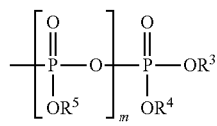

where
m=0 to 5, and
$R^1$ to $R^6$, independently of one another, are hydrogen, a metal, or $NR_zH_{4-z}^+$, where z and R are as described above, or an organic radical, wherein for said at least one inorganic phosphate X and $R^1$ to $R^5$ of formula (I) are not organic radicals, and for said at least one organic phosphate, either: (i) X is $R^6$, and $R^1$, $R^2$, and $R^6$ are organic radicals that may be the same or different, or (ii) X is according to formula (II), and $R^1$ to $R^5$ are organic radicals that may be the same or different,
component b) at least one compound comprising at least two hydroxyl groups and having a molecular weight of less than 250 g/mol, the proportion of component a), based on the composition, being from 0.1 to 70% by weight and the proportion of component b) being from 0.5 to 90% by weight, and
component c) an alkali metal hydroxide.

2. The composition according to claim 1, wherein said composition has a mass ratio of component a) to component b) of from 20:80 to 80:20.

3. The composition according to claim 1, wherein component b) is at least one compound selected from the group consisting of monoethylene glycol, diethylene glycol, triethylene glycol, tetraethylene glycol, propylene glycol, butylene glycol, glycerol, trimethylolpropane, and pentaerythritol.

4. The composition according to claim 1, wherein said organic radicals are independently selected from branched or straight-chained, acyclic or cyclic, alicyclic or heterocyclic, aliphatic or aromatic or heteroaromatic, substituted or unsubstituted, organic radicals or radicals of formula (III):

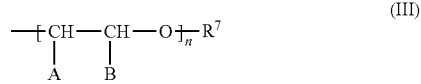

where
$R^7$=a branched or straight-chain, acyclic or cyclic, alicyclic or heterocyclic, aliphatic or aromatic or heteroaromatic, substituted or unsubstituted organic radical,
A or B is hydrogen and the respective other radical is hydrogen or a substituted or unsubstituted, linear or branched alkyl radical having 1 to 10 carbon atoms and n is a number-average number from 1 to 100.

5. The composition according to claim 1, wherein said at least one inorganic phosphate of formula (I) comprises an alkali metal polyphosphate and/or an alkali metal monophosphate and said at least one organic phosphate of formula I comprises dioleyl phosphate.

6. A process for the production of a composite moulding by continuous or batchwise compression moulding of a mass containing at least one organic binder and at least one material which is present in the form of chips, fibres, mats, powders or granules, said process comprising performing compression moulding in the presence of a release agent composition according to claim 1.

7. The process according to claim 6, wherein said organic binder comprises isocyanates, polyisocyanates, urea/formaldehyde, phenol/formaldehyde, melamine/formaldehyde, epoxy (EP), polyurethane, polyester and/or polylactide resins.

8. The process according to claim 6, wherein the release agent composition is applied to a compression mould and/or to a mass to be moulded.

9. The composition according to claim 1, further comprising from 80 to 98% by weight water.

* * * * *